United States Patent [19]
Merciadez et al.

[11] Patent Number: 5,354,902
[45] Date of Patent: Oct. 11, 1994

[54] STABILIZED SORBIC ACID OR SALT THEREOF

[75] Inventors: Mel Merciadez, Avenel; Kas Mohammed, Somerville; Francois Y. Maniere, Princeton Junction, all of N.J.

[73] Assignee: McNeil-PPC, Inc., Milltown, N.J.

[21] Appl. No.: 54,355

[22] Filed: Apr. 28, 1993

Related U.S. Application Data

[63] Continuation of Ser. No. 966,246, Oct. 26, 1992, abandoned.

[51] Int. Cl.$^5$ .......................................... C07C 51/377
[52] U.S. Cl. ............................................... 562/601
[58] Field of Search .................... 562/601; 252/400.53

[56] References Cited

U.S. PATENT DOCUMENTS

| | | | |
|---|---|---|---|
| 4,460,787 | 7/1984 | Coleman et al. | 562/601 X |
| 4,639,294 | 1/1987 | Kamei et al. | 562/601 X |
| 4,736,063 | 4/1988 | Coleman et al. | 562/601 X |
| 4,740,617 | 4/1988 | Hallcher | 562/601 X |

OTHER PUBLICATIONS

S. S. Arya et al., "Degradation Products of Sorbic Acid in Aqueous Solutions", Food Chemistry 29, (1988), pp. 41–49.

S. S. Arya, "Stability of Sorbic Acid in Aqueous Solutions", Journal of Agricultural and Food Chemistry, 28, (1980), 1246–1249.

L. Pekkarinen, "The Effects of Salts of Heavy Metals on the Stability of Sorbic Acid in Oxygenated Sulphuric Acid Solutions", Suomen Kemistilehti, 40, No. 2 (1967), 54–58.

L. Pekkarinen, "The Mechanism of Oxidation of Sorbic Acid by Molecular Oxygen in Water", Suomen Kemistilehti, 42, No. 3, (1969), 147–152.

J. N. Sofos, "Sorbate Food Preservatives", CRC Press, Inc., Boca Raton, Fla. (1989).

Pekkarinen, "The Influence of Metal Acetates on the Oxidation of Sorbic Acid by Molecular Oxygen in Acetic Acid and Comparison of the Results with Those for Eleostearic Acids", Acta Chemica Scandinavica, 26, (1972), 2367–2371.

Pekkarinen et al., "The Effects of Salts of Heavy Metals on the Stability of Sorbic Acid in Oxygenated Dilute Sulphuric Acid Solutions", Suomen Kemistilehti B, 40, No. 2, (1967), 54–58.

*Primary Examiner*—Arthur C. Prescott
*Attorney, Agent, or Firm*—Charles J. Metz

[57] ABSTRACT

Stabilized aqueous solutions containing sorbic acid or salt thereof in an antimicrobial proportion, and further containing from 0.1, and preferably from 0.2, to about 5 ppm of manganous ion, said manganous ion being in an amount sufficient to inhibit oxidation of said sorbic acid or salt thereof to oxidative products such as acetaldehyde.

21 Claims, 8 Drawing Sheets

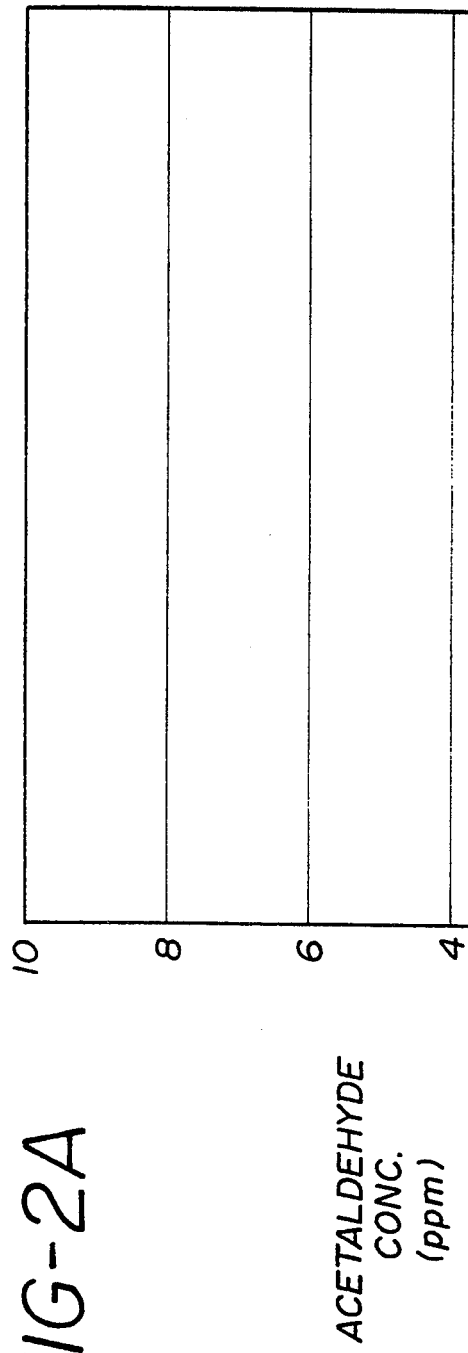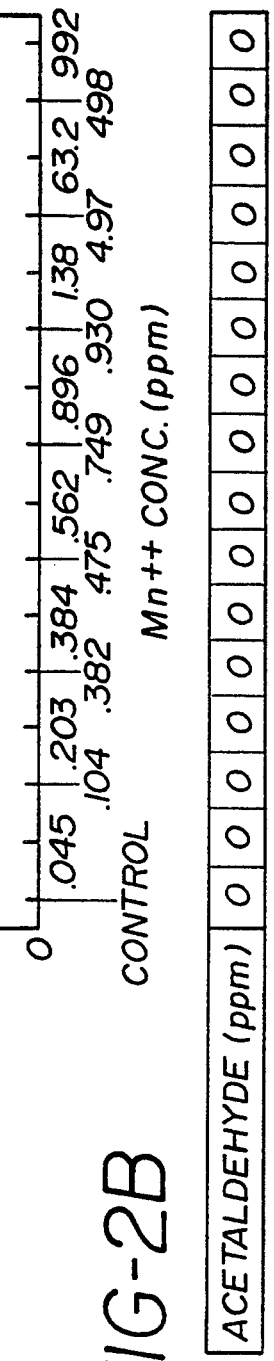
FIG-2A
FIG-2B

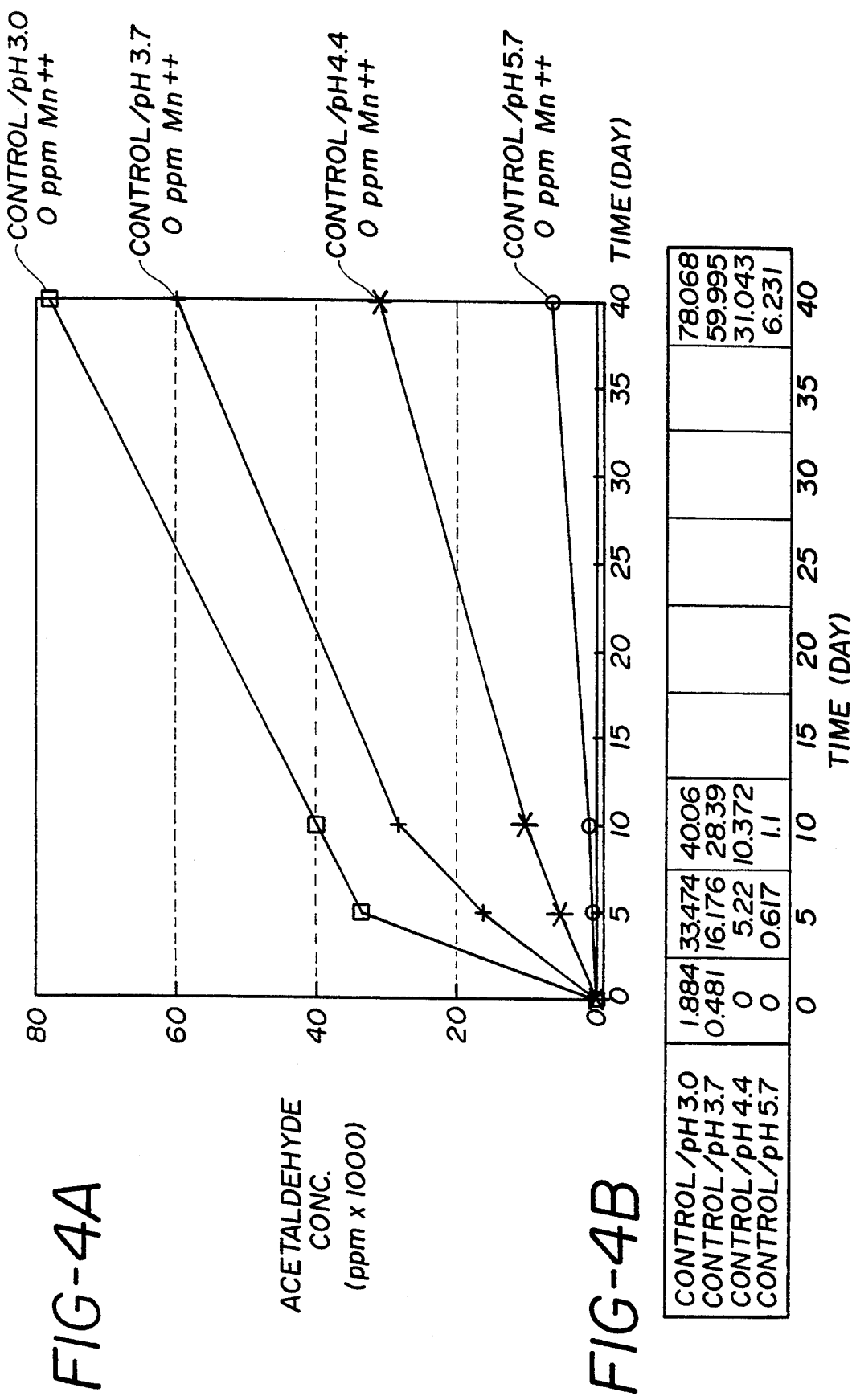

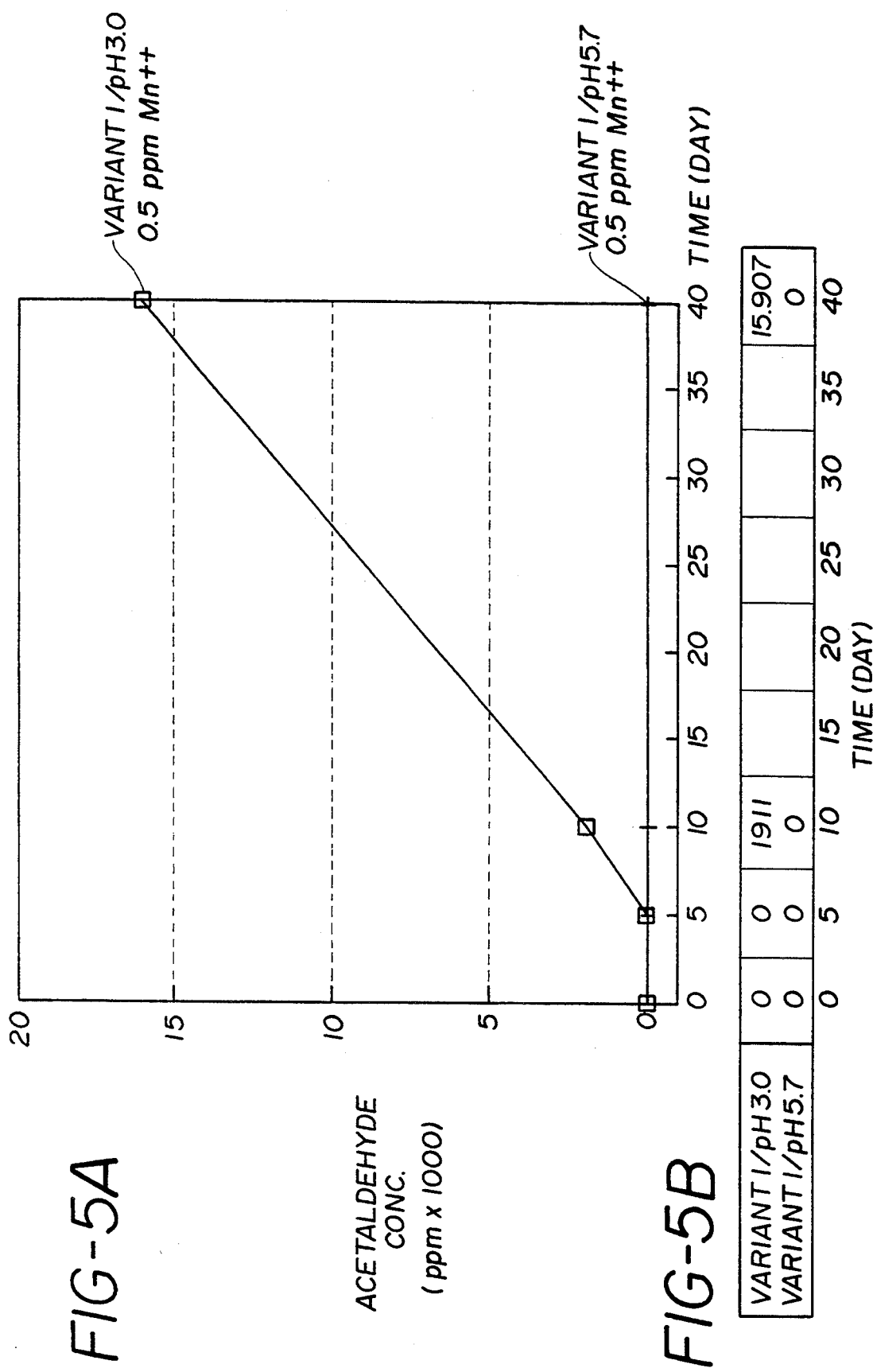

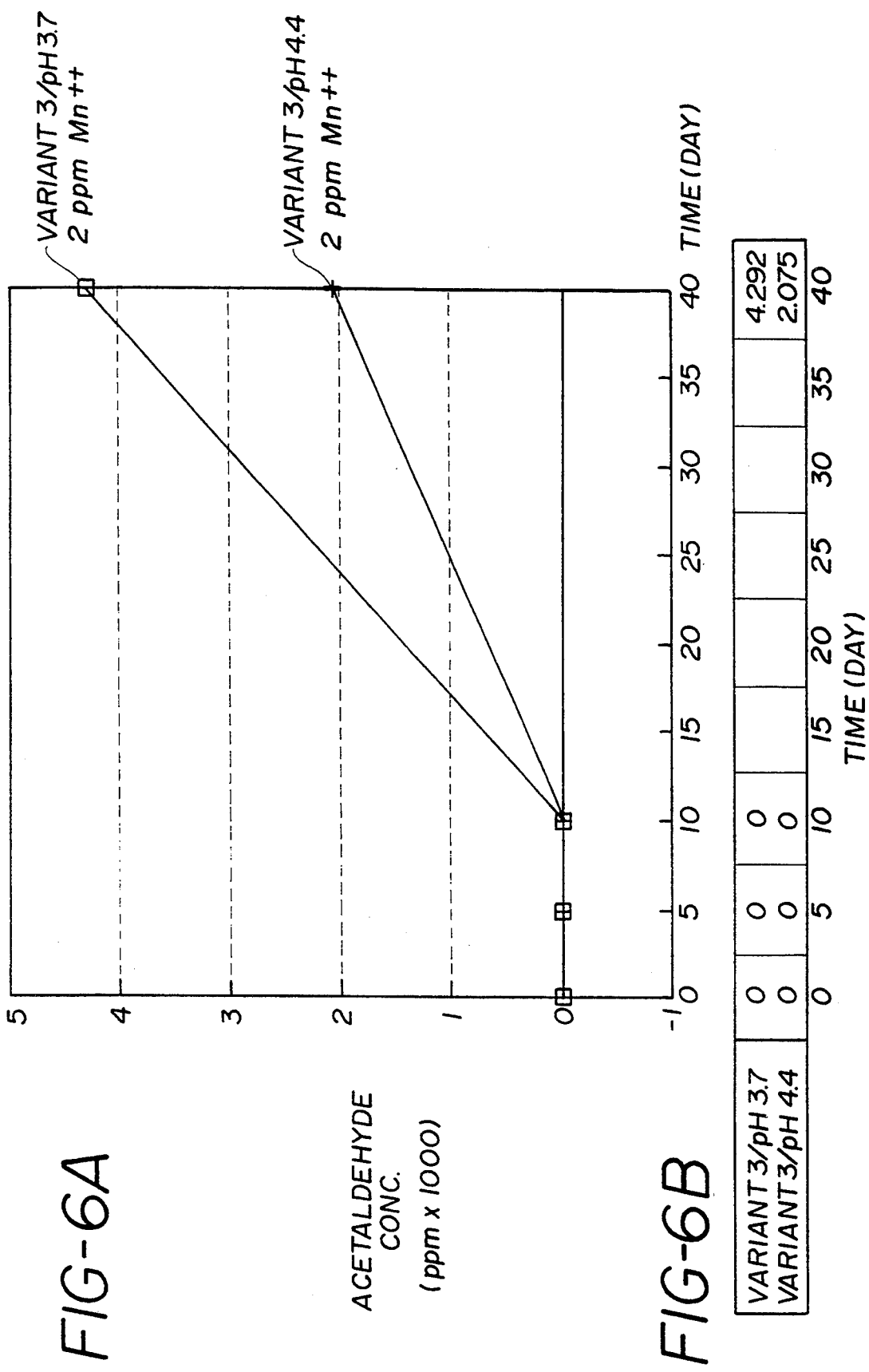

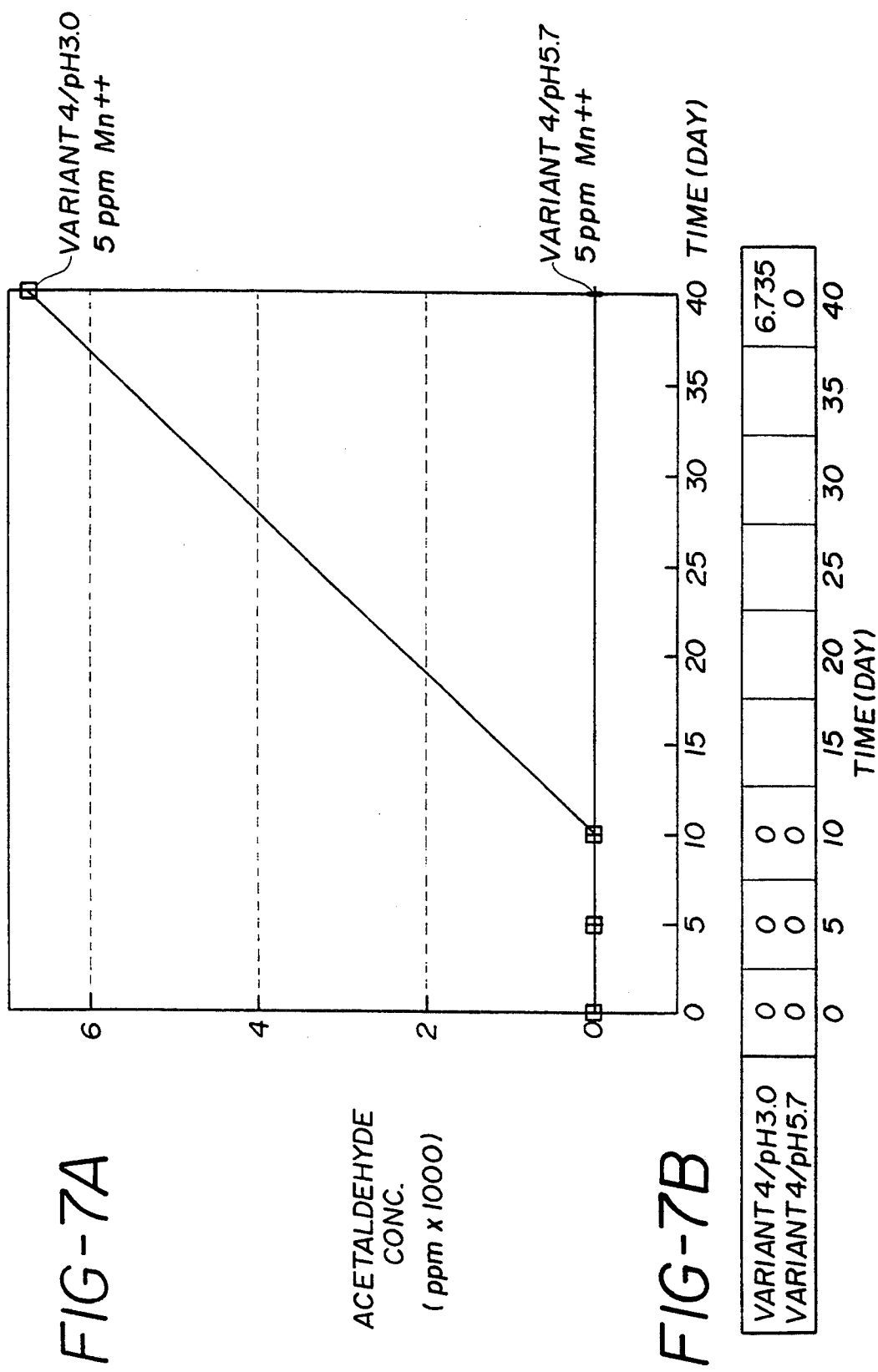

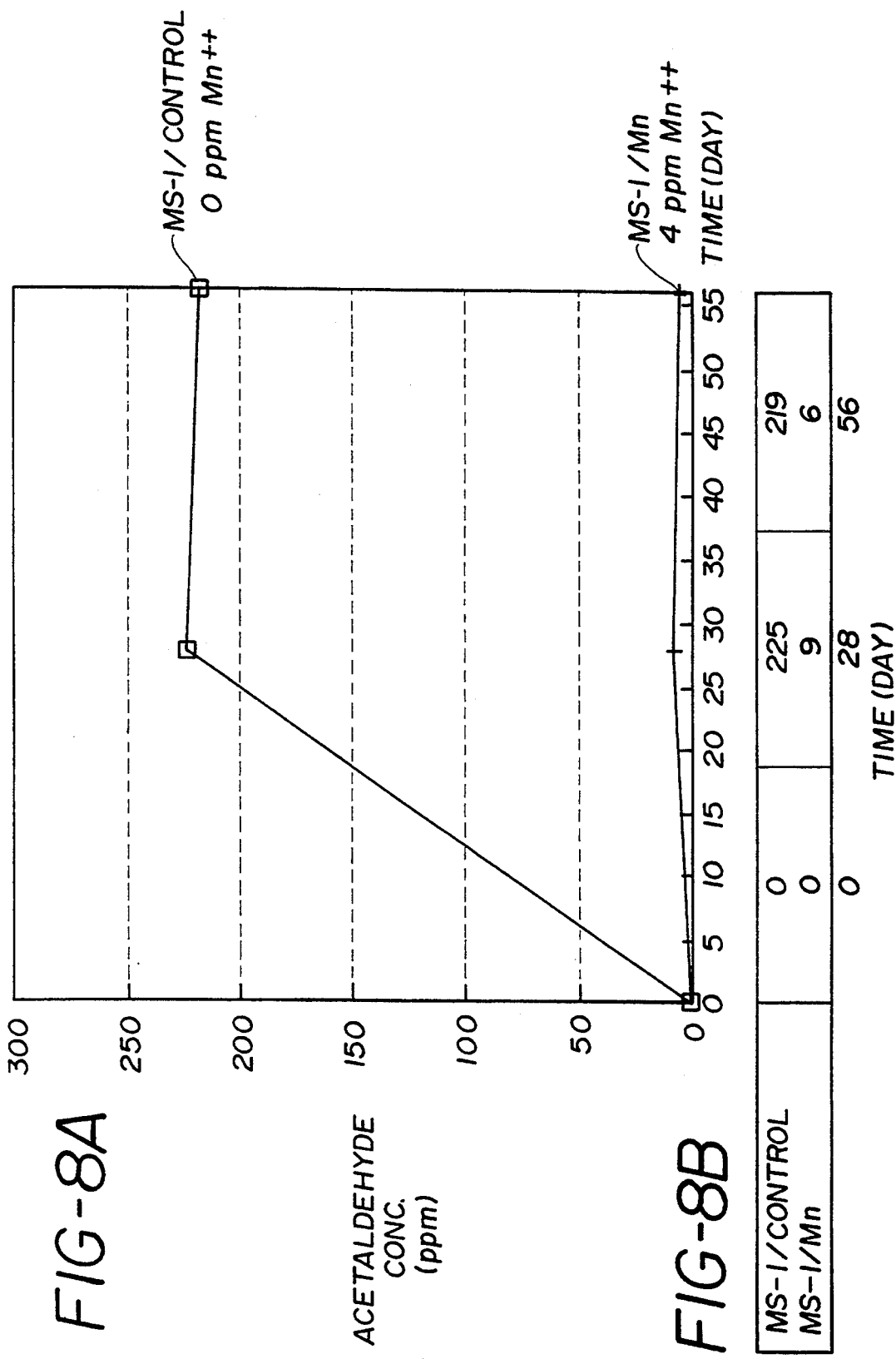

STABILIZED SORBIC ACID OR SALT THEREOF

This is a continuation of application Ser. No. 966,246, filed Oct. 26, 1992 now abandoned.

The invention relates to sorbic acid or salt thereof containing low concentrations of manganous ($Mn^{++}$) ion as a stabilizer.

BACKGROUND OF THE INVENTION

Sorbic acid (2,4-hexadienoic acid) and salts thereof, especially potassium sorbate, are widely used as antimicrobials in packaged foods and pharmaceutical and other health care products intended for human or animal use. Sorbic acid and salts thereof are particularly valuable as fungistatic agents to inhibit or retard the growth of molds and yeasts. Although sorbic acid and its salts are quite stable when dry, they are susceptible to oxidation in aqueous solution. This oxidation produces products such as ketones and aldehydes, which can cause development of undesired flavors or odors, and polymers of the aldehydes can cause development of undesired color. The oxidation of sorbic acid or salt thereof can result in the loss of sufficient sorbate ion to impair the desired antimicrobial effect.

The mechanism of oxidation of sorbic acid and means to stabilize against such oxidation have been the subject of considerable research. See, for instance, S. S. Arya et al., "Degradation Products of Sorbic Acid in Aqueous Solutions", Food Chemistry 29, (1988), pages 41–49; S. S. Arya, "Stability of Sorbic Acid in Aqueous Solutions", Journal of Agricultural and Food Chemistry, 28, (1980), 1246–1249; L. Pekkarinen et al., "THE EFFECTS OF SALTS OF HEAVY METALS ON THE STABILITY OF SORBIC ACID IN OXYGENATED SULPHURIC ACID SOLUTIONS", Suomen Kemistilehti, 40, No. 2, (1967), 54–58; L. Pekkarinen, "THE MECHANISM OF OXIDATION OF SORBIC ACID BY MOLECULAR OXYGEN IN WATER", Suomen Kemistilehti, 42, No. 3, (1969), 147–152; J. N. Sofos, "Sotbate Food Preservatives", CRC Press, Inc., Boca Raton, Fla. (1989); Pekkarinen, "The Influence of Metal Acetates on the Oxidation of Sorbic Acid by Molecular Oxygen in Acetic Acid and Comparison of the Results with Those for Eleostearic Acids", Acta Chemica Scandinavica, 26, (1972) 2367–2371; and Pekkarinen et al., "THE EFFECTS OF SALTS OF HEAVY METALS ON THE STABILITY OF SORBIC ACID IN OXYGENATED DILUTE SULPHURIC ACID SOLUTIONS", Suomen Kemistilehti B, 40, No 2., (1967) 54–58.

The above-cited authors have disclosed that heavy metal ions including manganous ($Mn^{++}$) ion have been used to stabilize sorbic acid and sorbate salts against oxidation. The proportions disclosed to be effective have been 50 ppm (parts, by weight, per million) [S. S. Arya] and $10^{-2}$ to $10^{-3}$ mol/l [about 55 to 550 milligrams of manganous ion per liter - Pekkarinen et al.]

The present invention is based upon the discovery that the presence of a very small proportion of manganous ion in aqueous solutions of sorbic acid or salt thereof is effective in stabilizing such aqueous solutions against oxidation.

BRIEF DESCRIPTION OF THE INVENTION

The invention provides stabilized aqueous solutions containing sorbic acid or salt thereof in an antimicrobial proportion, especially in a fungistatic proportion, and further containing from 0.1 and, preferably from 0.2, to about 5 ppm (parts, by weight, per million parts of solution) of manganous ion, said manganous ion being in an amount sufficient to inhibit or retard oxidation of said sorbic acid or salt thereof to oxidized products such as acetaldehyde. Acetaldehyde production is undesirable because it polymerizes (via an aldol reaction sequence) to form chromogens and there is a known correlation between acetaldehyde production and sorbate reduction [Arya et al. (1988); confirmed by the inventors herein].

BRIEF DESCRIPTION OF THE DRAWINGS

FIGS. 2A and 3A are graphs of acetaldehyde concentrations of the same aqueous solutions versus concentration of manganous ion, after storage at 50° C. for 5 and 10 days, respectively.

FIGS. 2B and 3B are tables of acetaldehyde concentrations of the same aqueous solutions containing various concentrations of manganous ion, after storage at 50° C. for 5 and 10 days, shown in the graphs in FIGS. 2A and 3A, respectively;

FIGS. 4A, 5A, 6A and 7A are graphs of acetaldehyde concentration of similar aqueous solutions (containing no sucralose) versus concentration of manganous ion, at various pH's, after storage at 50° C. for 0, 5, 10 and 40 days;

FIGS. 4B, 5B, 6B and 7B are tables of acetaldehyde concentration of the aqueous solutions (containing no sucralose) containing various concentrations of manganous ion, at various pH's, after storage at 50° C. for 0, 5, 10 and 40 days, shown in the graphs in FIGS. 4A, 5A, 6A and 7A, respectively;

FIG. 8A is a graph of acetaldehyde concentration of a fluoride containing mouthwash versus manganous ion concentration, after storage at 50° C. for 0, 28, and 56 days;

FIG. 8B is a table of acetaldehyde concentrations of the same fluoride containing mouthwash containing various manganous ion concentrations, after storage at 50° C. for 0, 28, and 56 days, shown in the graph in FIG. 8A;

FIG. 9 is a graph of percentage of original sorbate content remaining of the same fluoride containing mouthwash versus manganous ion concentration, after storage at 50° C. for 0, 28, and 56 days;

FIGS. 10 and 11 are graphs of, respectively, color development and % of original sorbate remaining, versus manganous ion concentration of aqueous sucralose concentrate solution containing potassium sorbate and various concentrations of manganous ion, after storage for 53 or 59 days at 50° C.; and FIGS. 12 and 13 are graphs of, respectively, % sorbate remaining and acetaldehyde concentration of a buffered sorbate-containing solution containing various concentrations of $Mn^{++}$ ion and at various pH values, after storage at 50° C.

DETAILED DESCRIPTION OF THE INVENTION

Figure 1A:
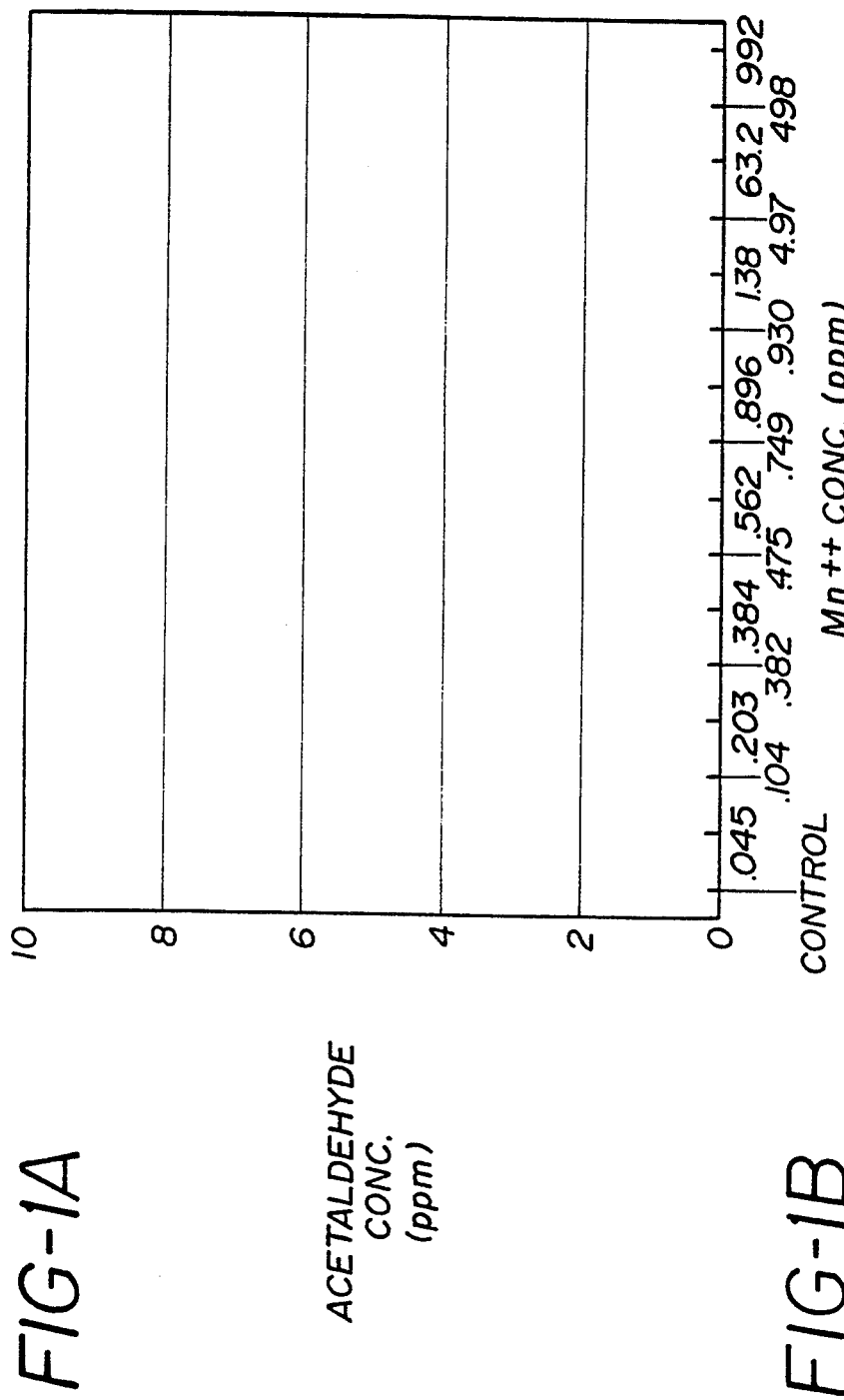
FIG. 1A is a graph of acetaldehyde concentrations of freshly prepared aqueous sucralose concentrate solutions containing potassium sorbate versus concentration of manganous ion.

The aqueous solutions of sorbic acid or salt thereof (typically potassium sorbate or other alkali metal salt) of the invention contain the sorbic acid or salt thereof in an antimicrobial proportion in an amount sufficient to inhibit or retard the growth of bacteria and, preferably, molds and yeasts, in the solution. Such amounts are usually within the range of from about 0.005% (unless otherwise indicated, all percentages given herein are by weight, based upon the total weight of the solution) to about 5%. It is preferred to employ potassium sorbate because of its good solubility in aqueous compositions and because it is generally recognized as safe for use in foods and other products, such as mouth washes, dental rinses, cough syrups, tonics, condiments, syrups, jams and jellies, carbonated and still beverages, aqueous-based ointments and lotions, and the like, that are intended for human and animal use.

The manganous ion can be added to the solution in any convenient manner, for instance by adding a soluble manganous salt such as manganese sulfate (MnSO4) to the solution. The amount of added manganous salt should be sufficient to provide from 0.1, and preferably from 0.2, to about 5 ppm of $Mn^{++}$ ion to the solution. An alternative method of adding the $Mn^{++}$ ion is to pass the solution to be stabilized by sotbate through a bed of activated charcoal containing manganous ion so that the ion leaches out into the solution in the desired amount (and preferably add the sorbate after the treatment with activated charcoal, since the charcoal may absorb significant amounts of sorbate).

A preferred composition of the invention comprises aqueous liquid concentrates of sucralose, a high intensity sweetener whose chemical name is 4-chloro-4-deoxy-α-D-galactopyranosyl-1,6-dichloro1,6-dideoxy-β-D-fructofuranoside. Such aqueous liquid concentrates contain from 3 to 35 weight percent (and preferably from 20 to 28 weight percent) sucralose, a preservative system including sorbic acid or salt thereof, a buffering system to maintain a pH of about 4 to 5.5, water, and from 0.1, and preferably from 0.2, to about 5 parts, by weight, per million parts of solution, of $Mn^{++}$ ion. Such aqueous liquid concentrates (without the manganous ion) are disclosed by Antenucci et al., EP-A-0,493,919, published on Jul. 8, 1992.

Other stabilized aqueous solutions of the invention include mouth washes, dental rinses, cough syrups, tonics, condiments, syrups, jams and jellies, carbonated and still beverages, ointments and lotions, and the like, containing sorbic acid or salt thereof as a preservative and from 0.1, and preferably from 0.2, to about 5 parts, by weight, per million parts of solution of manganous ion.

EXAMPLE 1

In order to demonstrate the invention, various concentrations of $Mn^{++}$ ion (added as manganese sulfate monohydrate), were added to aqueous solutions of the following formulation:

| Ingredient | % by Weight |
| --- | --- |
| sucralose | 25.000 |
| potassium sorbate | 0.110 |
| sodium benzoate | 0.110 |
| citric acid, anhydrous | 0.272 |
| sodium citrate, dihydrate | 0.258 |
| purified water | 74.250 |
| | 100.000 |

The pH of the aqueous solution was 4.4.

Figure 1B:
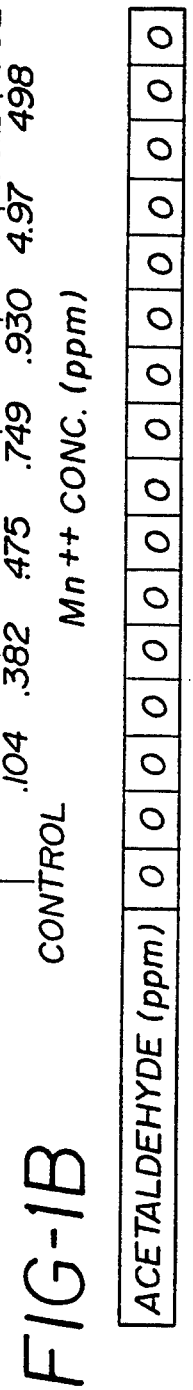
FIG. 1B is a table of acetaldehyde concentrations in the same freshly prepared aqueous sucralose concentrate solutions containing potassium sorbate, for the several concentrations of manganous ion, shown in the graph of FIG. 1A.
Figure 3A:
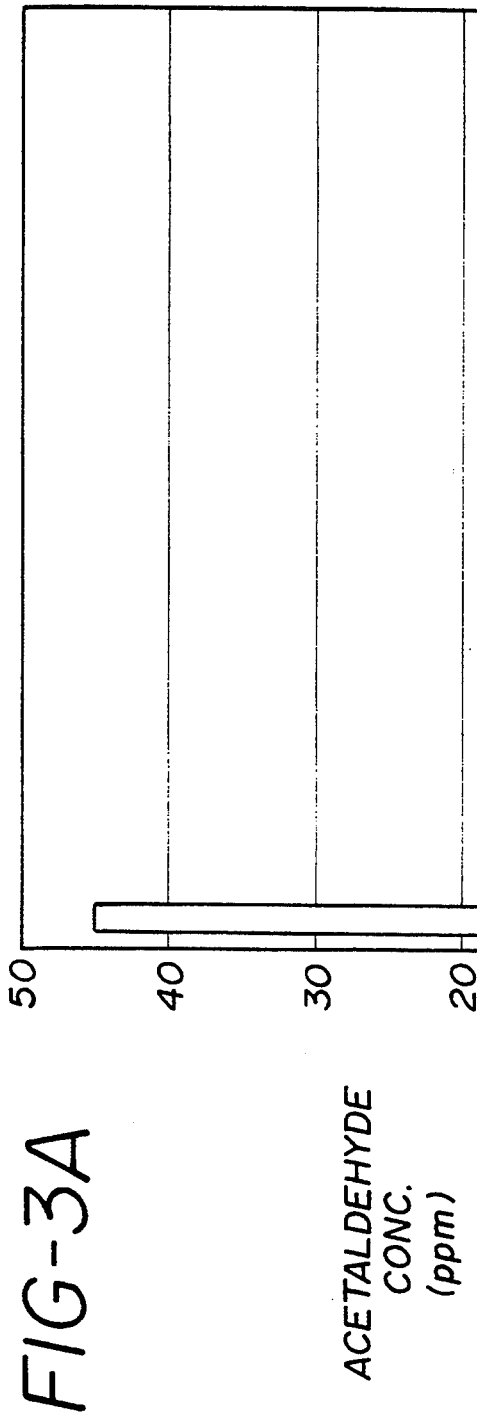
Figure 3B:
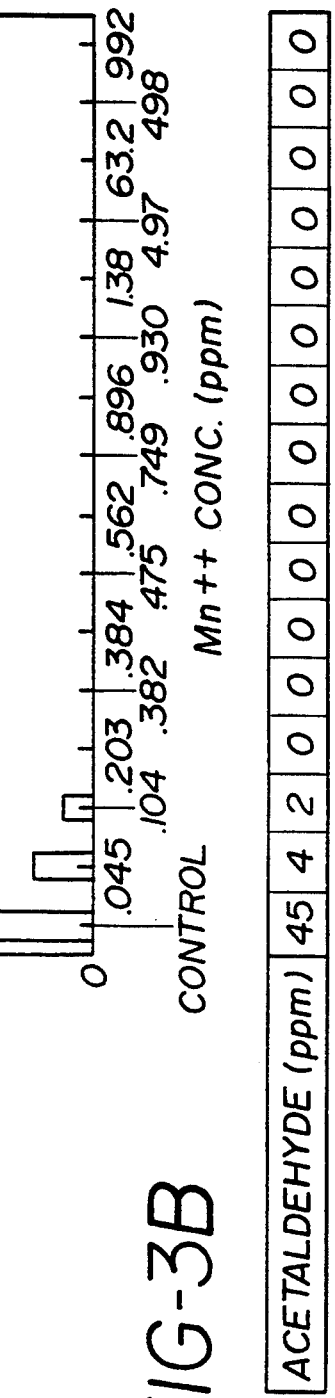

The several solutions were analyzed for acetaldehyde content by head space gas chromatography at day 0 (i.e., freshly prepared) and after storage at 50° C. for 5 and 10 days. The results are shown in FIGS. 1–3. As can be seen from the results, the samples containing 0.2 ppm or more $Mn^{++}$ ion contained no detectable acetaldehyde after 10 days.

Other analyses showed that the samples containing about 500 (by analysis, 498) and about 1000 (by analysis, 992) ppm $Mn^{++}$ ion began to lose sorbate content after 5 days (sorbate contents were 0.09% after 5 days and 0.08% after 10 days). These samples also began to develop color after 5 days. The initial APHA [American Public Health Association] color of the 1000 ppm $Mn^{++}$ sample had been 10–20; after 5 days this sample's color was 20–30 and after 10 days it was 30–40. The initial APHA color of the 500 ppm $Mn^{++}$ sample was 5–10; after 5 days it was 10–20 and after 10 days it was 20–30.

The samples containing about 5 and 63 ppm $Mn^{++}$ had initial APHA colors of 5–10, both of which were unchanged after 5 days but had APHA colors of 10–20 after 10 days. These samples did not lose sorbate content after 10 days. All the other samples, including the control, were unchanged as to color and sorbate content after 10 days.

The percent of original sorbate remaining and the color development analyses of samples containing a wide range of $Mn^{++}$ concentrations after 59 days at 50° C. are shown in FIGS. 10 and 11, respectively.

EXAMPLE 2

The following experiments were carried out to further illustrate the invention:

Potassium sorbate samples were dissolved in equal weight portions of deionized water to produce 50% (w/w) aqueous solutions. Manganous sulfate monohydrate ($MnSO_4.H_2O$) was added in proportions (by weight) as shown in the following table (the actual quantities used, in grams, are shown in parentheses):

| | K Sorbate | $Mn^{++}$ | $MnSO_4.H_2O$ |
| --- | --- | --- | --- |
| Control | 1100 (250) | 0 | 0 |
| Variant 1 | 1100 (250) | 0.5 | 1.54 (0.350) |
| Variant 3 | 1100 (250) | 2 | 6.15 (1.398) |
| Variant 4 | 1100 (250) | 5 | 15.36 (3.49) |

(A Variant 2, which contained 1 ppm $Mn^{++}$, was prepared but was not tested.)

The solutions were transferred into freeze drying trays, frozen, and then freeze dried by the following procedure:

Precautions must be taken in freeze drying potassium sorbate as it may sublime at temperatures above 60° C. (Solos, 1989). Pour the solution of potassium sorbate and manganese sulfate in the freeze drying trays and include temperature probes. Place trays on the freeze dryer shelf, the temperature of which has been set to −40° C. or below. When the samples are frozen, turn the condenser on and set to −45° C. or below. Turn the vacuum on and allow vacuum to reach 100 mTorr or less. Turn shelf heat on and set its temperature to −8° C. When the sample temperature equilibrates to −8° C., raise the shelf temperature to 10°-12° C. When the sample temperature reaches 10°-12° C., raise the shelf temperature to 25° C. Once the temperature of the samples has reached 25° C., the samples are dry. This procedure takes about 24-36 hours to complete, depending on the depth of the sample solution in the trays.

The freeze dried potassium sorbate samples containing various concentrations of $Mn^{++}$ were dissolved in acidified, buffered aqueous solutions of the following formulation:

| INGREDIENT | PERCENT (w/w) |
| --- | --- |
| Sodium benzoate | 0.110 |
| Potassium sorbate (plus $Mn^{++}$) | 0.110 |
| Citric acid, anhydrous | 0.272 |
| Sodium citrate, dihydrate | 0.258 |
| Sodium hydroxide, 50% aqueous solt'n | As needed for targeted pH |
| Purified water | To yield 100 |
| Total | 100 |

The following table presents the pH values for the several solutions and the APHA color development at 50° C. at Day 0 and after 5, 10 and 40 days:

| Sample | ppm $Mn^{++}$ | pH | APHA COLOR DEVELOPMENT AT 50° C. | | | |
| --- | --- | --- | --- | --- | --- | --- |
| | | | Day 0 | Day 5 | Day 10 | Day 40 |
| Control | 0 | 3.0 | 0-5 | 0-5 | 30-40 | 100-120 |
| Control | 0 | 3.7 | 0-5 | 0-5 | 30-40 | 90-100 |
| Control 0 | 0 | 4.4 | 0-5 | 0-5 | 20-30 | 90-100 |
| Control 0 | 0 | 5.7 | 0-5 | 0-5 | 5-10 | 30-40 |
| Var. 1 | 0.5 | 3.0 | 0-5 | 0-5 | 0-5 | 5-10 |
| Var. 1 | 0.5 | 5.7 | 0-5 | 0-5 | 5-10 | 0-5 |
| Var. 3 | 2 | 3.7 | 0-5 | 0-5 | 5-10 | 5-10 |
| Var. 3 | 2 | 4.4 | 0-5 | 0-5 | 0-5 | 5-10 |
| Var. 4 | 5 | 3.0 | 0-5 | 0-5 | 5-10 | 5-10 |
| Var. 4 | 5 | 5.7 | 0-5 | 0-5 | 5-10 | 5-10 |

The samples were also tested for acetaldehyde concentration at days 0, 5, 10 and 40; the results are displayed in FIGS. 4-7.

This Example 2 illustrates an important aspect of the invention wherein potassium sorbate is intimately mixed with manganous ion, said manganous ion being present in an amount sufficient to inhibit oxidation of said potassium sorbate to acetaldehyde when said potassium sorbate is dissolved in aqueous solution. Illustrations of useful sorbate:$Mn^{++}$ proportions are within the range of from about 11,000:1 to about 200:1, by weight.

The data presented in this Example 2 further illustrates the fact that the pH of the aqueous solution is an important parameter to be considered when practicing the invention. As the data indicates, at higher pH values such as 5.7, the rate of oxidation to form color and acetaldehyde is lower than at a pH of about 3. This is illustrated in the graphs presented as FIGS. 12 and 13, which are graphs of, respectively, % sorbate remaining and acetaldehyde concentration of a buffered sorbate-containing solution containing various concentrations of $Mn^{++}$ ion and at various pH values, after storage at 50° C.

EXAMPLE 3

An alcohol-free, fluoride dental mouthwash was prepared from the following ingredients:

| Ingredient | % W/W | Grams |
| --- | --- | --- |
| Na Fluoride, USP | 0.05 | 1.00 |
| Na Phosphate, dibasic (dihydrate) | 0.063 | 1.26 |
| Na Phosphate, monobasic (anhydrous) | 0.10 | 2.00 |
| Tween 80 (polysorbate 80, NF) | 0.10 | 2.00 |
| Na Saccharin, USP | 0.10 | 2.00 |
| Potassium Sorbate, NF | 0.25 | 5.00 |
| Pluronic F-127 (Poloxamer-407) | 1.00 | 20.00 |
| Sorbitol Solution, USP (70%) | 8.00 | 160.00 |
| Flavor (optional) | — | — |
| Colorant (optional) | — | — |
| Purified Water, USP q.s. to 100% | — | 1806.74 |
| Total | 100.00 | 2000.00 |

Two variants were stored at 50° C. for 28 days; the control was a solution of the above formulation, the example of the invention contained 4 ppm of $Mn^{++}$ ion. The two samples were tested for color development, with the following results:

| Sample | | Day 0 | Day 28 |
| --- | --- | --- | --- |
| MS-1/Control | (0 ppm $Mn^{++}$) | 0-5 | 80-100 |
| MS-1/Mn | (4 ppm $Mn^{++}$) | 0-5 | 5-10 |

The two stored samples were also tested for acetaldehyde concentration and for percent of original sorbate remaining at days 0, 28, and 56. The results are displayed in FIGS. 8 and 9, respectively.

What is claimed is:

1. A stabilized aqueous solution containing sorbic acid or salt thereof in an antimicrobial proportion, and further containing from 0.1 to about 5 parts, by weight, per million parts of solution of manganous ion, said manganous ion being in an amount sufficient to inhibit oxidation of said sorbic acid or salt thereof to acetaldehyde.

2. The solution of claim 1 wherein the solution contains from 0.2 to about 5 parts, by weight, per million parts of solution of manganous ion.

3. The solution of claim 1 wherein said solution contains potassium sorbate.

4. The solution of claim 2 wherein said solution contains potassium sorbate.

5. The solution of claim 1 further containing sucralose.

6. The solution of claim 2 further containing sucralose.

7. The solution of claim 3 further containing sucralose.

8. The solution of claim 4 further containing sucralose.

9. The stabilized aqueous solution of claim 1 wherein said solution is an aqueous mouthwash.

10. The aqueous mouthwash of claim 9 further containing fluoride.

11. Freeze dried potassium sorbate containing manganous ion in an amount sufficient to inhibit oxidation of said potassium sorbate to acetaldehyde when said potassium sotbate is dissolved in aqueous solution.

12. An intimate mixture of potassium sorbate and manganous ion, said manganous ion being present in an amount sufficient to inhibit oxidation of said potassium sorbate to acetaldehyde when said potassium sorbate is dissolved in aqueous solution.

13. The stabilized aqueous solution of claim 1 wherein said solution is a dental rinse.

14. The stabilized aqueous solution of claim 1 wherein said solution is a cough syrup.

15. The stabilized aqueous solution of claim 1 wherein said solution is a carbonated beverage.

16. The stabilized aqueous solution of claim 1 wherein said solution is a non-carbonated beverage.

17. The stabilized aqueous solution of claim 1 wherein said solution is a jam.

18. The stabilized aqueous solution of claim 1 wherein said solution is a jelly.

19. The stabilized aqueous solution of claim 1 wherein said solution is a syrup.

20. The stabilized aqueous solution of claim 1 wherein said solution is an aqueous-based ointment.

21. The stabilized aqueous solution of claim 1 wherein said solution is an aqueous-based lotion.

* * * * *